(12) United States Patent
Nowrouzieh et al.

(10) Patent No.: US 8,887,553 B2
(45) Date of Patent: Nov. 18, 2014

(54) APPARATUS FOR DETERMINING THE INTER-FIBER FRICTIONAL COEFFICIENT

(76) Inventors: Shahram Nowrouzieh, Gorgan (IR); Jean-Yves Drean, Mulhouse cedex (FR); Artan Sinoimeri, Mulhouse cedex (FR)

( * ) Notice: Subject to any disclaimer, the term of this patent is extended or adjusted under 35 U.S.C. 154(b) by 380 days.

(21) Appl. No.: 13/348,659

(22) Filed: Jan. 12, 2012

(65) Prior Publication Data

US 2013/0180313 A1  Jul. 18, 2013

(51) Int. Cl.
*G01N 19/02* (2006.01)

(52) U.S. Cl.
USPC .................................. 73/9; 73/159

(58) Field of Classification Search
CPC ....................................... G01N 19/02
USPC ............................................. 73/9, 159
See application file for complete search history.

(56) References Cited

U.S. PATENT DOCUMENTS

| | | | | |
|---|---|---|---|---|
| 3,376,730 A | * | 4/1968 | Webb | 73/9 |
| 4,194,387 A | * | 3/1980 | Hofbauer et al. | 73/9 |
| 5,490,410 A | * | 2/1996 | Markstrom | 73/9 |
| 6,349,587 B1 | * | 2/2002 | Mani et al. | 73/9 |
| 2009/0320555 A1 | * | 12/2009 | Ebrecht | 73/9 |
| 2013/0047699 A1 | * | 2/2013 | Padgurskas et al. | 73/7 |

* cited by examiner

*Primary Examiner* — Hezron E Williams
*Assistant Examiner* — Nashimya Fayyaz
(74) *Attorney, Agent, or Firm* — Barry Choobin; Patent 360 L.L.C.

(57) ABSTRACT

Disclosed is an apparatus for determining the inter-fiber frictional coefficient of staple fibers. The apparatus comprises a pair of clamps, one fixed and the other mobile wherein, each clamp receives an end portion of a sliver therewithin. The apparatus further comprises a pair of predetermined weights, each mounted over a clamp in order to exert normal force on either end of the sliver whereby the movement of the sliver within the clamps is resisted as the mobile clamp is moves away from the fixed clamp until the sliver is severed off, a force sensor for sensing the tensile force exerted by the sliver, and a means for computing the inter-fiber frictional coefficient, which is a function of the normal force and the amount of tensile force exerted by the sliver which overcomes the inter-fiber frictional force of the sliver.

19 Claims, 8 Drawing Sheets

Apparatus

APPARATUS FOR DETERMINING THE INTER-FIBER FRICTIONAL COEFFICIENT

BACKGROUND OF THE INVENTION

1. Field of the Invention

The present invention relates to material testing devices and apparatuses, and more particularly to an apparatus for determining the inter-fiber frictional coefficient of staple fibers.

2. Background Art

The study of parameters that contribute to the strength of yarn is one of the major areas of interest in the textile industry world over. One such parameter is the inter-fiber frictional coefficient of staple fibers, which are processed into a yarn. A frictional coefficient is a dimensionless scalar value which describes the ratio of the force of friction between two bodies and the force pressing them together. Staple fibers are categorized as visco-elastic materials, and the coefficient of friction between two visco-elastic materials ranges between the values 0.66 and 1.

It has been scientifically established that: at low levels of inter-fiber frictional force, the yarn strength is equivalent to the inter-fiber frictional force, at moderate levels of inter-fiber frictional force, the yarn strength depends on the tensile strength of the fibers and the inter-fiber frictional force, and at high levels of inter-fiber frictional force, the tensile strength of the fibers is equivalent to the yarn strength. Based on this principle, since, as mentioned before, the inter-fiber frictional coefficient is low for visco-elastic materials, it could be stated that the maximum frictional force exerted by staple fibers in a sliver is equal to the tensile force or strength thereof.

SUMMARY OF THE INVENTION

The present invention comprises an apparatus for determining the inter-fiber frictional coefficient. The apparatus broadly comprises a means for determining the tensile force exerted by a sliver, and a means for computing the inter-fiber frictional coefficient based on the tensile force.

The means for determining the tensile force comprises a pair of clamps—one fixed and the other mobile, wherein each clamp receives an end portion of a sliver therewithin. A pair of predetermined weights, each of which is placed over a clamp so as to exert normal force on the end portion that is received therewithin. Once the weights are in place, the mobile clamp is drawn away from the fixed clamp until the sliver is severed off. A force sensor is employed for measuring the tensile force exerted by the sliver as the mobile clamp is drawn away from the fixed clamp.

The means for determining the inter-fiber frictional coefficient comprises a computer associated with the force sensor. Once the sliver is severed off, the computer computes the inter-fiber frictional coefficient, which is a function of the weights and the inter-fiber frictional force, which, as discussed above, is equal to the tensile strength of the sliver. More particularly, the amount of tensile force required to calculate the inter-fiber frictional coefficient is the maximum amount of tensile force exerted by the portion of the sliver held between the clamps.

The objects and advantages of the embodiments herein will become readily apparent from the following detailed description taken in conjunction with the accompanying drawings.

FIGURES—REFERENCE NUMERALS

10 . . . Apparatus
12 . . . Fixed Clamp
14 . . . Mobile Clamp
16 . . . Rail
20 . . . Top Component
22 . . . Bottom Component
24 . . . Longitudinal Depression
26 . . . Vertical Groove
28 . . . Top Panel
30 . . . Side Panel
32 . . . Radial Ball Bearing
34 . . . Downward Projection
36 . . . Sliver
38 . . . Predetermined Weight
40 . . . Crosshead
42 . . . Cable
44 . . . Pulley
46 . . . Force Sensor
48 . . . Displacement Sensor
50 . . . Computer

DETAILED DESCRIPTION OF A PREFERRED EMBODIMENT

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

Figure 1:
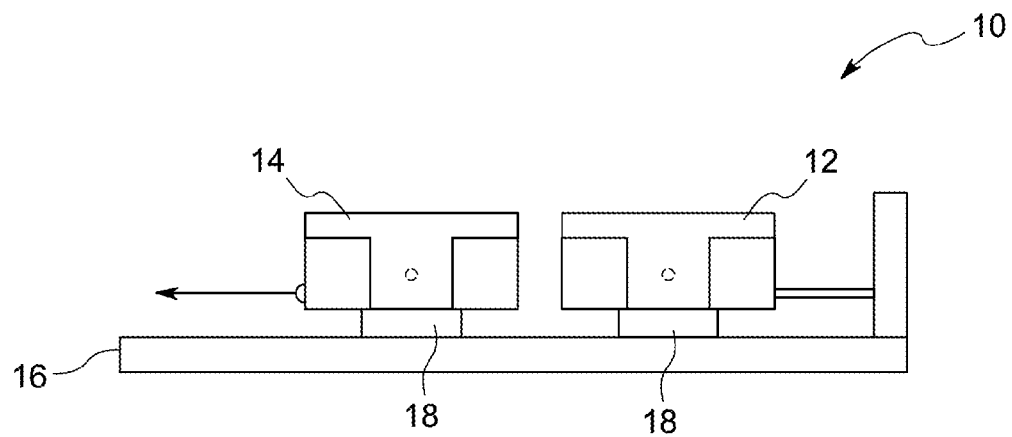
FIG. 1 is a schematic primarily depicting the pair of clamps of the apparatus of the present invention.
Figure 2:
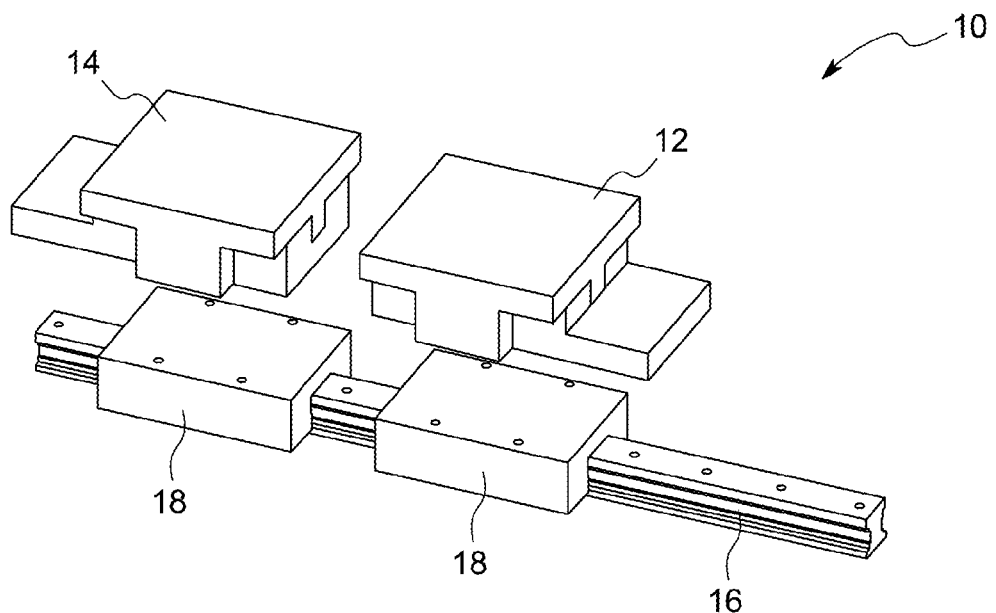
FIG. 2 is an exploded view of the pair of clamps and the linear guides mounted over the rail in accordance with the present invention.

The present invention comprises an apparatus 10 for determining inter-fiber frictional coefficient or coefficient of friction between staple fibers, which are processed into a yarn by spinning. Referring to FIGS. 1 and 2, the apparatus 10 comprises a pair of clamps comprising a fixed and a mobile clamp 12 and 14, each preferably made of aluminum. Each clamp is mounted over a rail 16 about a linear guide 18. While the position of the fixed clamp 12 is apparently fixed, the mobile clamp 14 is configured to slide over the rail 16 towards and away from the fixed clamp 12 about the linear guide 18 thereof The materials of the rail 16 and the linear guides 18, especially the linear guide 18 pertaining to the mobile clamp 14, are chosen such that the coefficient of friction therebetween is substantially low, for instance, between 300 mN to 800 mN. Periodically, lubricant can be applied between the rail 16 and the linear guide 18 of the mobile clamp 14 to further lessen the friction therebetween.

Figure 3:
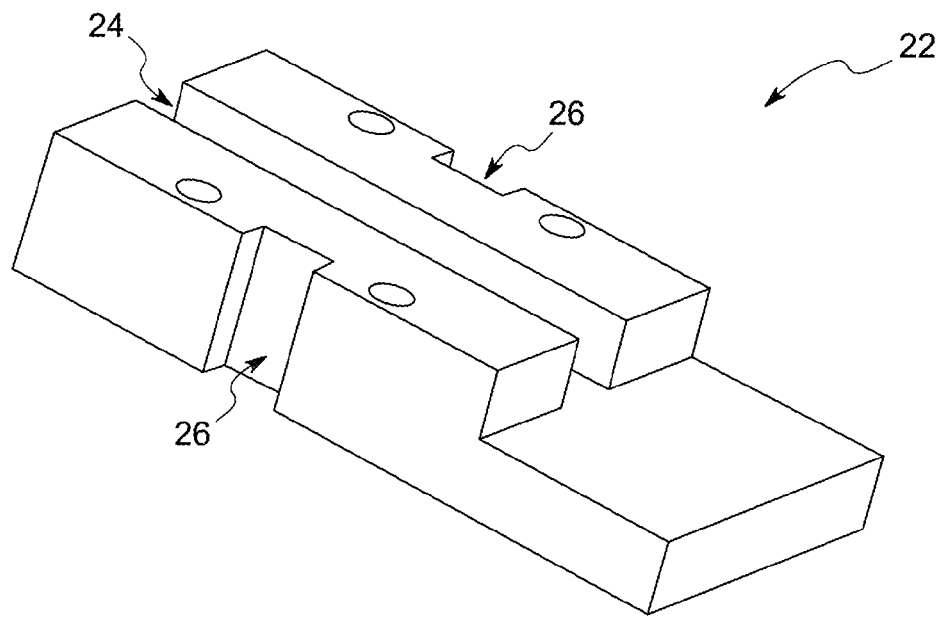
FIG. 3 is a perspective view of the bottom panel according to the present invention.

Each clamp comprises independent, rectangular top and bottom components 20 and 22. Referring to FIG. 3, the top surface of the bottom component 22 comprises a centrally-disposed, thorough, longitudinal depression 24 of uniform U-shaped cross-section, which lies parallel to the rail 16. Either side of each bottom component comprises a thorough vertical groove 26 of uniform U-shaped cross-section. The rear of the bottom component 22 comprises a rectangular extension comprising planar top and bottom surfaces. The thickness of the rectangular extension is lesser than the rest of the bottom component 22 thereby making the bottom component 22 a stepped structure.

Figure 4:
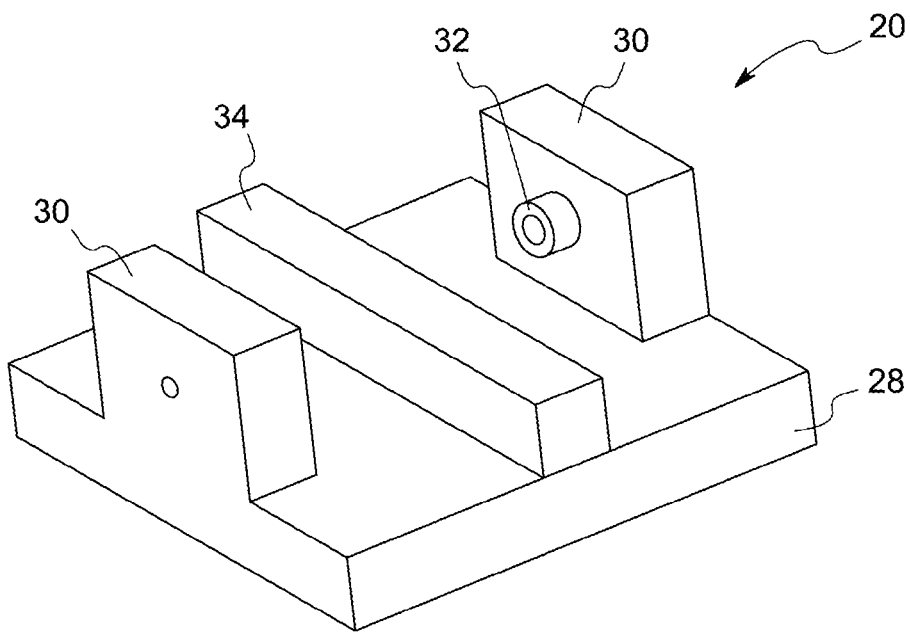
FIG. 4 is a perspective view of the top component according to the present invention; the top component resting on the top panel thereof.

Referring to FIG. 4, the top component 20 comprises a rectangular top panel 28 comprising a substantially planar top surface, a pair of vertical side panels 30 extending centrally downwardly from either side of the top panel 28, a pair of radial ball bearings 32, each attached to the inner surface of a side panel 30, and a downward projection 34 extending centrally from the bottom surface of the top panel 28. Each side panel 30 is centrally disposed as the length thereof is lesser than that of the side of the top panel 28 from which the side panel 30 extends. The top component 20 is dimensioned such that the axis passing through centers of the radial ball bearings 32 aligns with the planar, rectangular bottom surface of the projection 34 as seen in FIG. 5.

Figure 5:
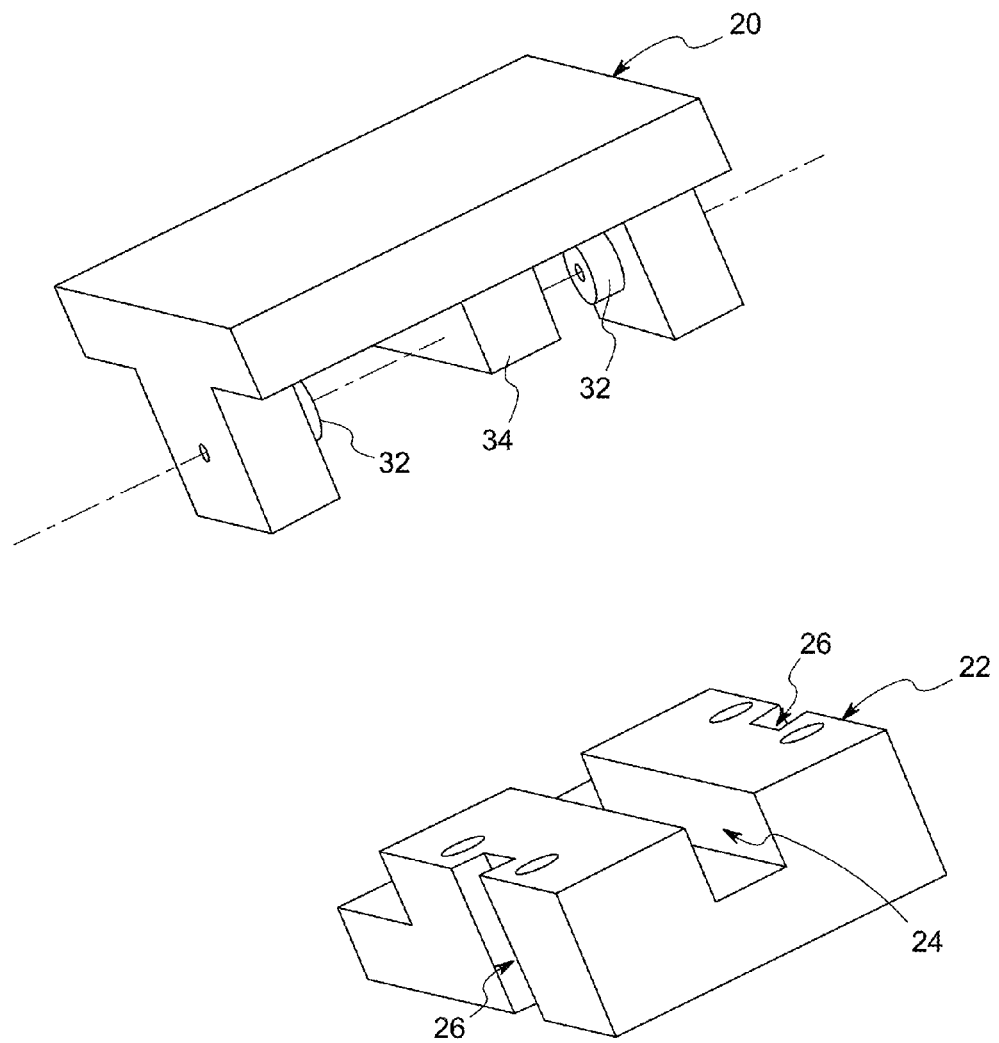
FIG. 5 is an exploded view of a clamp in accordance with the present invention.

Referring to FIG. 5, in order to combine the top and bottom components 20 and 22 together to form a clamp, the radial ball bearings 32 are received within the vertical grooves 26 whereby, the radial ball bearings 32 can vertically reciprocate within the vertical grooves 26. The downward projection 34 is received snugly within the longitudinal depression 24 as the top component 20 is received over the bottom component 22. The top and bottom components 20 and 22 are configured such that a slight gap is maintained between the bottom surface of the downward projection 34 and the surface of the longitudinal depression 24.

Figure 6:
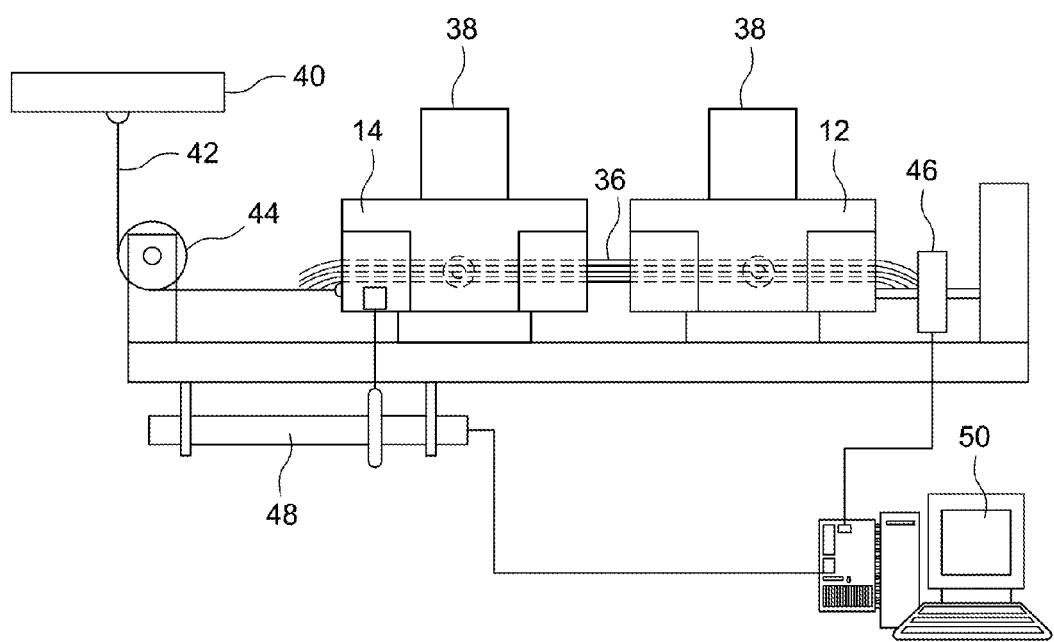
FIG. 6 is a schematic of the apparatus of the preset invention.

Referring to FIG. 6, the end portions of a sliver 36 are received within the longitudinal depressions 24 of the pair of clamps 12 and 14 in zero gauge position; a sliver 36 comprises a strand of loose fibers. Upon the placement of the end portions of the sliver 36 within the longitudinal depressions 24, the top components 20 are placed over the bottom components 22. A pair of predetermined weights 38, each of which is mounted over a clamp whereby, the end portions of the sliver 36 are held substantially tight within the pair of clamps 12 and 14.

In The Detailed Description of A Preferred Embodiment

Still referring to FIG. 6, once the weights 38 are in place, the mobile clamp 14 is drawn away from the fixed clamp 12 with a constant speed until the sliver 36 is severed off. More particularly, the mobile clamp 14 is drawn by a crosshead 40 about a cable 42 through a pulley 44. The crosshead 40 pertains to a tensile tester, preferably MTS20 tensile tester. The apparatus 10 further comprises a force sensor 46 for measuring and recording the tensile force exerted by the portion of the sliver 36 held between the pair of clamps 20 and 22. The force sensor 46 is a zero stability sensor that works based on metal foil strain gauges. Preferably, the force sensor is an ELFS-T3 from Entran. The apparatus further comprises a displacement sensor 48 for measuring and recording the displacement of the mobile clamp 14 right from the point where the mobile clamp 14 is idle till the point where the sliver 36 is severed off. More particularly, the displacement sensor 48 is an absolute position measurement differential transformer. The force and displacement sensors 46 and 48 are associated with a computer 50, which calculates the inter-fiber frictional coefficient as a function of the predetermined weights 38 and the amount of frictional force, which is same as the amount of tensile force at which, the portion of the sliver held between the clamps 20 and 22 begins to stretch.

Figure 7:
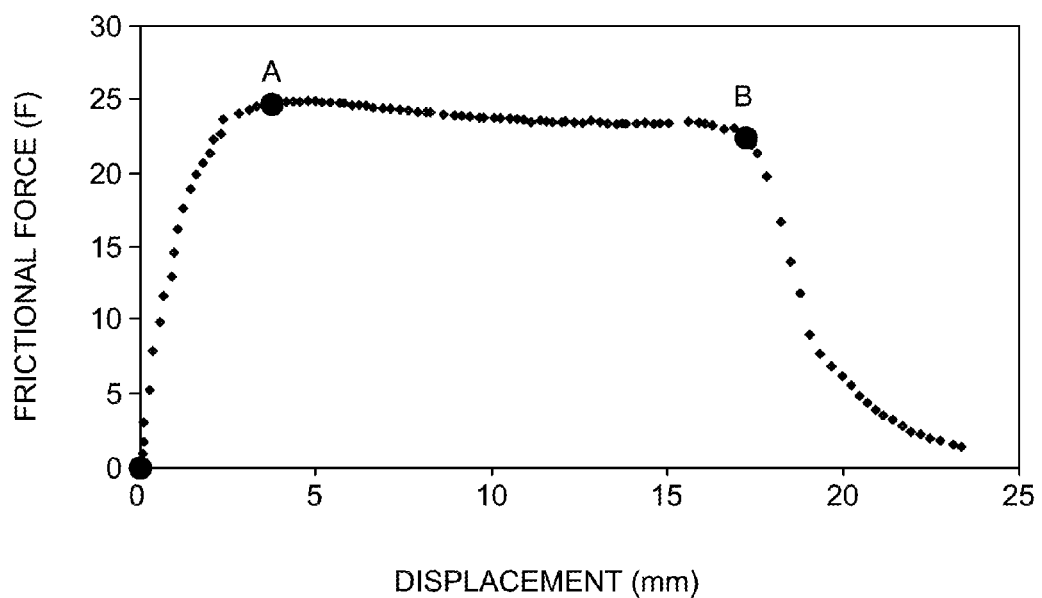
FIG. 7 is a graphical representation of the tensile force exerted by the sliver with respect to the displacement of the mobile clamp.

Referring to FIGS. 7 and 8, the OA portion of the graph indicates the straightening of the portion of the sliver 36 held between the clamps as the mobile clamp 14 is drawn away from the fixed clamp 12. At point O, the clamps are at the position shown in the FIG. 8A, and at point A, the clamps 12 and 14 are the position shown in FIG. 8B where, it can be noticed that the portion of the sliver 36 held between the clamps is substantially straightened out. At point A, as can be noticed in the graph, the tensile force exerted the portion of the sliver 36 held between the clamps is maximum.

Figure 8A:
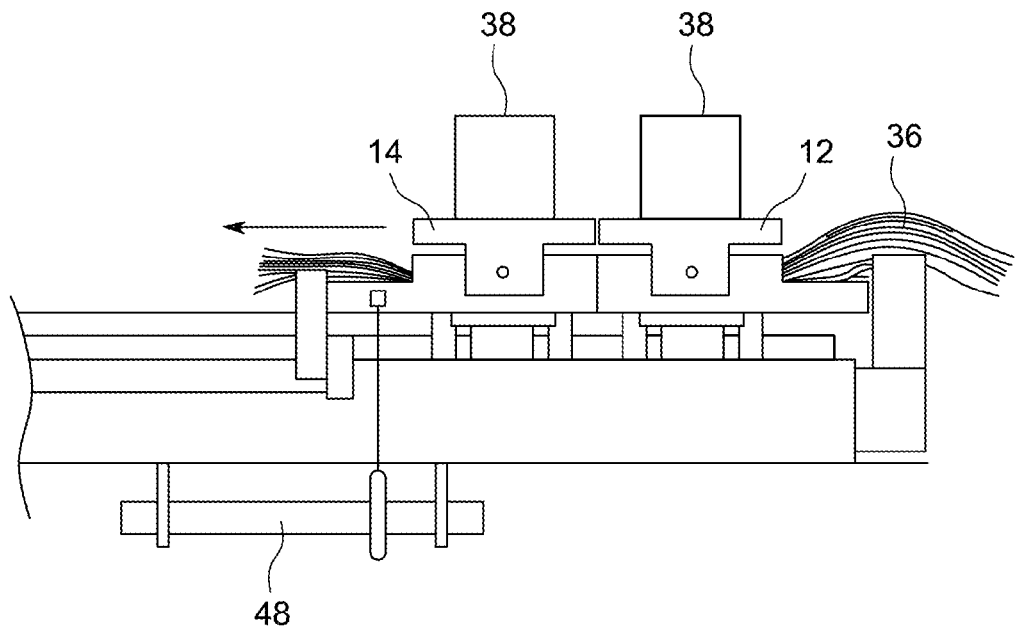
FIG. 8 shows the sequential events involved as the sliver is being subjected to tensile stress.
Figure 8B:
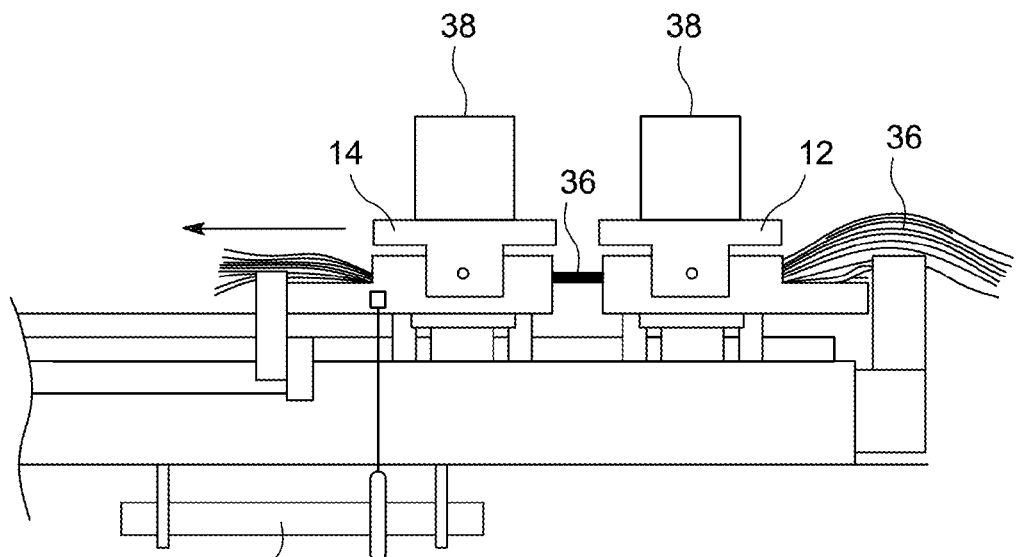
Figure 8C:
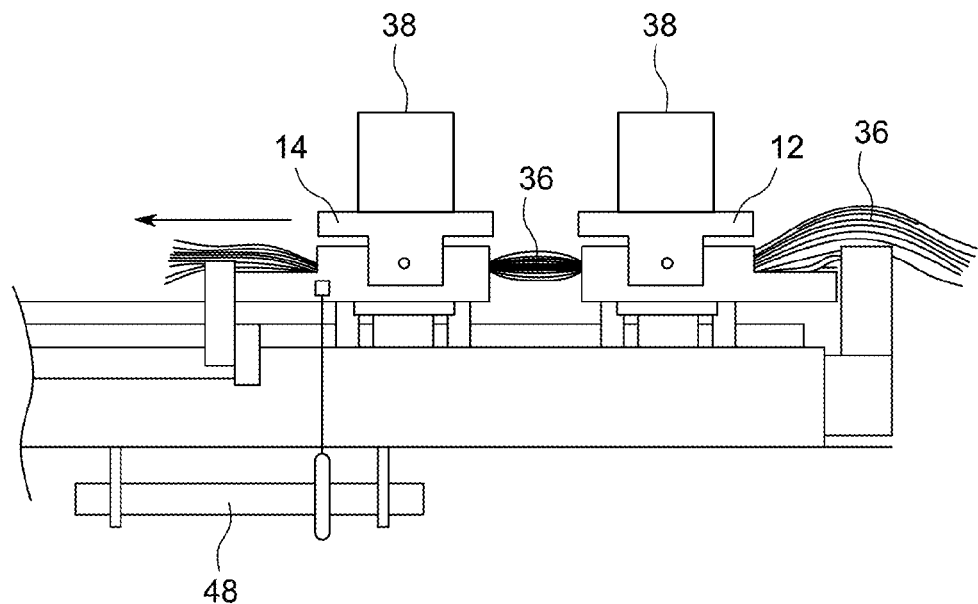
Figure 8D:
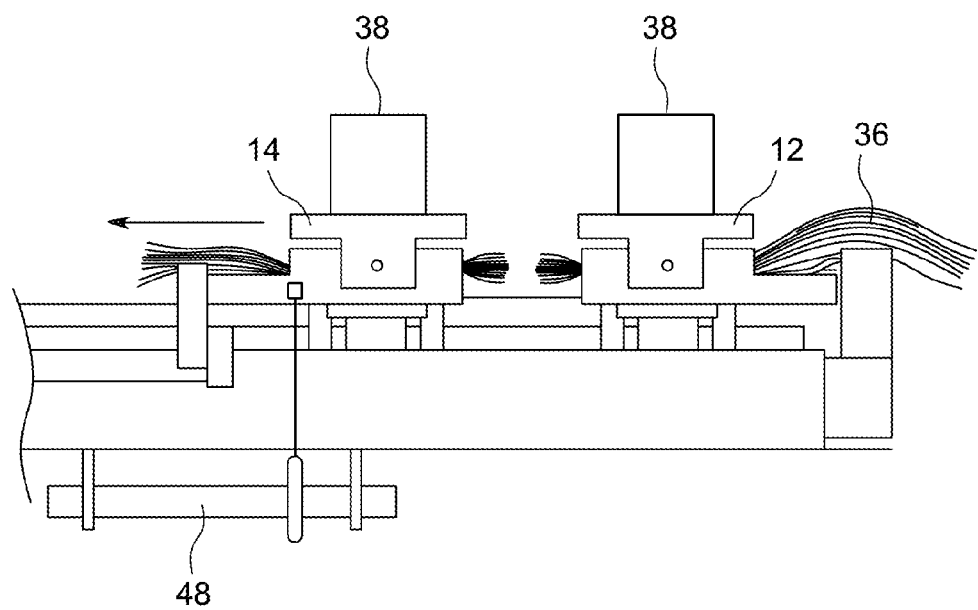

Still referring to FIGS. 7 and 8, post point A, the portion of the sliver 36 between the clamps begins to stretch as seen in FIG. 8C. During the AB phase of the graph, the portion of the sliver 36 held between the clamps begins to bulge and finally at point B the sliver 36 begins to sever off as can be viewed in FIG. 8D. Since the sliver 36 from point B begins to weaken, the tensile force from the point B begins to decline till the value thereof reaches nil.

Still referring to FIGS. 7 and 8, the amount of tensile force required for the calculation of the inter-fiber frictional coefficient is same as the amount of tensile force that overcomes the frictional resistance of the fibers in the sliver 36 thereby causing the fibers in the sliver 36 to stretch as seen in FIG. 8C. As can be seen in the graph, the stretching of the fibers commences from the point A, and therefore, the amount of tensile force required for the calculation of the inter-fiber frictional coefficient is the same amount of tensile force exerted by the sliver at point A.

As previously discussed, since the coefficient of friction between visco-elastic materials is low, the tensile strength of the same equals the frictional force thereof. As the staple fibers are categorized as visco-elastic materials, it could be said that the tensile strength of the sliver 36 is equal to the frictional force thereof. The following is the equation for determining the inter-fiber frictional force:

$$F = S a m^{1-n} W^n$$

where, F denotes the inter-fiber frictional force, S denotes the shear strength of the asperities, a denotes a material coefficient, m denotes the number of fibers in the sliver, W denotes the normal force, and finally, n denotes the inter-fiber frictional coefficient. The values of S and a and m are constant and are stored in a database associated with the computer 50, the value of W can be obtained from the weights 38, and finally, the value of F can be obtained from the force sensor 46. Once the values are in place, the value of n—the inter-fiber frictional coefficient—can be determined by the computer 50 on the basis of the following equation that is derived from the above equation:

$$n = {}^{W/m}\sqrt{\frac{F}{S\alpha m}}$$

Figure 9:
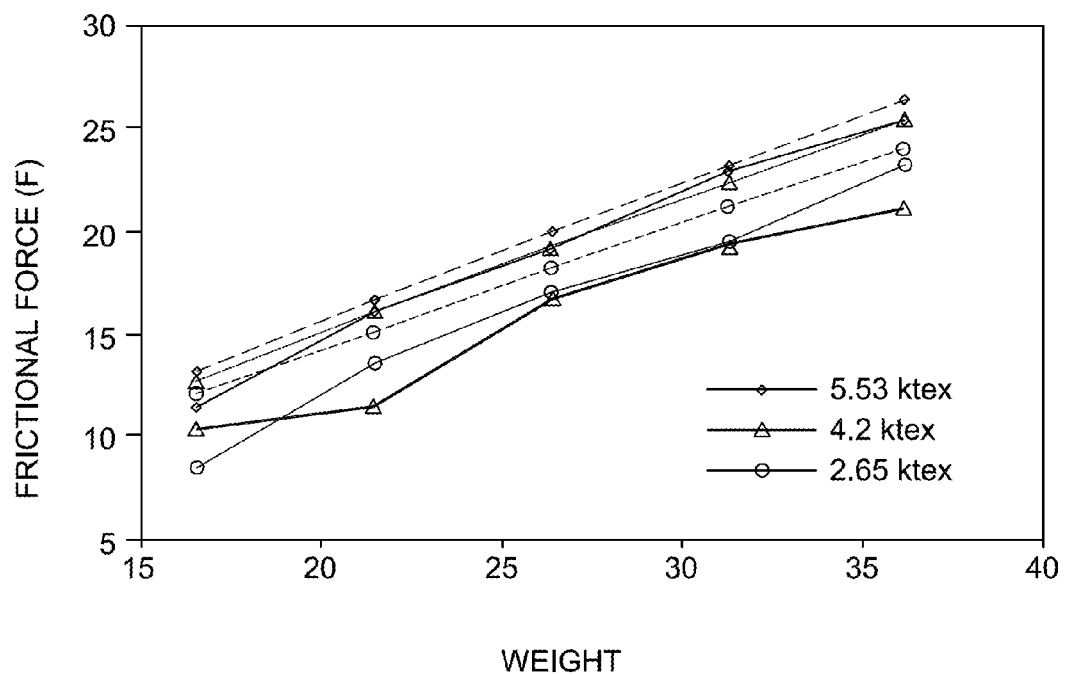
FIG. 9 is a graphical representation of inter-fiber frictional force of slivers of different counts with respect to weight.

The apparatus of the present invention can be tested for different sliver counts, weights, and speeds. For example, FIG. 9 shows the frictional behavior of three different counts of slivers, viz., 2.65, 4.20, and 5.53 ktex, under five different weights that are chosen between 1687.6 and 3687.6 grams. The mean inter-fiber frictional coefficient obtained for the aforesaid combination of sliver counts and weights is 0.866.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. An apparatus for determining the coefficient of friction between staple fibers, which are to be processed into a yarn, the apparatus comprising:
   (a) a pair of clamps comprising a fixed clamp and a mobile clamp, each clamp adapted to receive an end portion of a sliver of the staple fibers therewithin;
   (b) a pair of predetermined weights, each mounted over a the fixed clamp and the mobile clamp in order to exert normal load or force on either end of the sliver whereby the movement of the sliver between the fixed clamp and the mobile clamp is resisted as the mobile clamp is drawn away from the fixed clamp, the mobile clamp to be drawn away until the sliver is severed off;
   (c) a force sensor for sensing the tensile force exerted by the sliver as the mobile clamp is being drawn away from the fixed clamp; and
   (d) a means for computing the coefficient of friction, which is a function of the normal force and the amount of tensile force exerted by the sliver which overcomes an inter-fiber frictional force of the sliver, wherein the normal force is obtained from the pair of predetermined weights.

2. The apparatus of claim 1 wherein, the amount of tensile force required for computing the coefficient of friction is the maximum tensile force exerted by the sliver.

3. The apparatus of claim 1 wherein, the amount of tensile force required for computing the coefficient of friction is the same amount of tensile force at which the portion of the sliver held between the clamps begins to stretch, wherein the sliver beginning to stretch is determined by a computer.

4. The apparatus of claim 3 further comprising a displacement sensor for sensing and recording the displacement of the mobile clamp; the displacement sensor, along with the force sensor, associated with the computing means.

5. The apparatus of claim 1 wherein, the computing means comprises the computer.

6. The apparatus of claim 1 wherein, the coefficient of friction is also a function of the number of fibers in the sliver and the shear strength of the asperities; the values of the number of fibers and the shear strength are constant and are stored within a database associated with the computing means.

7. The apparatus of claim 1 further comprising a rail whereon the mobile clamp is slidably mounted.

8. The apparatus of claim 7 wherein, the frictional force between the mobile clamp and the rail range between 300 mN to 800 mN.

9. The apparatus of claim 1 wherein, each clamp is made of aluminum.

10. The apparatus of claim 1 wherein, each clamp comprises:
   (a) a bottom component comprising a longitudinal depression of uniform cross-section within which an end portion of the sliver is received;
   (b) a top component comprising a downward projection that snugly fits into the depression whereby the sliver in the depression is held substantially tight when one of the predetermined weights is mounted over the top component.

11. The apparatus of claim 10 wherein, the top component comprises a horizontal top panel, a pair of side panels extending downward from either side of the top panel, a pair of radial ball bearings connected to a vertical inner side of each side panel wherein, the pair of radial ball bearings are slidably received within a pair of vertical grooves disposed on either side of the bottom component whereby, the top component is slidably received over the bottom component.

12. The apparatus of claim 1 wherein, the force sensor comprises a zero stability sensor.

13. The apparatus of claim 1 wherein, the force sensor works based on metal foil strain gauges.

14. The apparatus of claim 1 wherein, the movement of the mobile clamp is enabled by a crosshead of a tensile testing machine driven by a software application; the mobile clamp connected to the crosshead by a cable.

15. The apparatus of claim 14 wherein, the tensile testing machine comprises MTS20M tensile testing machine.

16. The apparatus of claim 14 wherein, the software application comprises Test Works 4 software.

17. The apparatus of claim 1 wherein, the end portions of the sliver are placed in a zero gauge position within the clamps.

18. The apparatus of claim 1 wherein, the mobile clamp is drawn away from the fixed clamp with a predetermined speed.

19. An apparatus for determining the coefficient of friction between staple fibers, which are to be processed into a yarn, the apparatus comprising:
   (a) a rail;
   (b) a pair of clamps comprising a fixed clamp and a mobile clamp, the mobile clamp slidably mounted over the rail, each clamp comprising:
      (i) a bottom component comprising a thorough longitudinal depression of uniform cross-section within which an end portion of the sliver of the staple fibers is received in a zero gauge position, and a pair of vertical grooves disposed on either side thereof; and (ii) a top component comprising a horizontal top panel, a downward projection that snugly fits into the depression, a pair of side panels extending downward from either side of the top panel, and pair of radial ball bearings connected to a vertical inner side of each side panel wherein, the pair of radial ball bearings are slidably received within the pair of vertical grooves whereby, the top component is slidably received over the bottom component;

(c) a pair of predetermined weights, mounted over the pair of clamps in order to exert normal load or force on either end portions of the sliver whereby, the movement of the sliver within the clamps is resisted as the mobile clamp is drawn away from the fixed clamp, the mobile clamp to be drawn away with a predetermined speed until the sliver is severed off;

(d) a force sensor for sensing the tensile force exerted by the sliver as the mobile clamp is being drawn away from the fixed clamp; and (e) a computer for computing the coefficient of friction, which is a function of the number of fibers in the sliver, the shear strength of the asperities of the fibers, the normal force, and the amount of tensile force exerted by the sliver at which the portion of the sliver held between the clamps begin to stretch; the values of the number of fibers and the shear strength are constant and are stored within a database associated with the computer, wherein the normal force is obtained from the pair of predetermined weights.

* * * * *